United States Patent [19]
Dufresne et al.

[11] Patent Number: 4,926,864
[45] Date of Patent: May 22, 1990

[54] BIOLOGICAL TISSUE STIMULATOR WITH TIME-SHARED LOGIC DRIVING OUTPUT TIMING AND HIGH VOLTAGE STEP-UP CIRCUIT

[75] Inventors: Joel R. Dufresne; Alan P. Dieken, both of St. Paul, Minn.

[73] Assignee: Minnesota Mining and Manufacturing Company, St. Paul, Minn.

[21] Appl. No.: 361,784

[22] Filed: May 30, 1989

Related U.S. Application Data

[63] Continuation of Ser. No. 42,166, Apr. 24, 1987, abandoned.

[51] Int. Cl.$^5$ .............................................. A61N 1/32
[52] U.S. Cl. .................................................... 128/421
[58] Field of Search ........... 128/419 R, 419 E, 419 D, 128/419 PG, 419 PS, 421, 422, 423 R, 423 W

[56] References Cited

U.S. PATENT DOCUMENTS 3,258,013  6/1986  Druz ................................ 128/419 D
3,653,387  4/1972  Ceier ................................ 128/419 D
3,667,477  6/1972  Susset et al. .................... 128/419 E
3,886,950  6/1975  Ukkestad et al. .............. 128/419 D
4,031,899  6/1977  Renirie .......................... 128/419 PS
4,632,117 12/1986  James .
4,665,920  5/1987  Campbell .......................... 128/422

FOREIGN PATENT DOCUMENTS 3109489  9/1982  Fed. Rep. of Germany ... 128/419 D Primary Examiner—Ruth S. Smith
Attorney, Agent, or Firm—Donald M. Sell; Walter N. Kirn; William D. Bauer

[57] ABSTRACT

A biological tissue stimulator having a time-shared logic element alternately supplying switching signals to a step-up voltage circuit powered from a low-voltage power source and supplying a plurality of amplitude timing signals to an output circuit utilizing the high-voltage output from the step-up voltage circuit. A high-voltage storage device is utilized to store the voltage generated in the step-up voltage circuit until it can be utilized by the output circuit.

10 Claims, 5 Drawing Sheets

BIOLOGICAL TISSUE STIMULATOR WITH TIME-SHARED LOGIC DRIVING OUTPUT TIMING AND HIGH VOLTAGE STEP-UP CIRCUIT This is a continuation of application Ser. No. 042,166, filed Apr. 24, 1987, now abandoned.

BACKGROUND OF THE INVENTION

The present invention relates generally to biological tissue stimulators and relates more particularly to biological tissue stimulators having high-voltage output circuits.

Biological tissue stimulators are known to be medically useful. In one example, transcutaneous electrical nerve stimulators (TENS) are utilized to mask pain signals in a human body before they reach the brain giving the subject apparent relief from pain. In such TENS devices, electrical pulses, usually current pulses of a selected rate, amplitude, pulse width and duty cycle, are delivered to the skin of the subject by one or more electrodes. The timing characteristic of the delivered pulses may be predetermined, as for example, by the prescribing physician and/or may be individually selected or controlled by switches available to be operated by the subject. Additionally, individual parameters, or even entire pulse programs, can be varied in a predetermined or random basis by the TENS device itself.

Another example of useful biological tissue stimulators are neuromuscular stimulators (NMS) which can be utilized to electrically stimulate muscle activity of a patient. In such neuromuscular stimulators electrical pulses, again probably current pulses of a carefully controlled rate, amplitude, pulse width and sequence are delivered by electrodes to a site or sites near the muscle to be stimulated in order to activate or contract the muscle. The initiation and control of such sequence of pulses may be patient controlled.

In both of these biological tissue stimulators, an output stage supplies electrical pulses having certain timing and amplitude characteristics. The amplitude of these electrical current pulses is usually of a substantial, e.g., 10–100 milliamperes, current level. Such current levels are achievable by means of a high-voltage power supply, e.g., 40 to 100 volts. The logic circuits necessary for supplying the timing and amplitude information are typically powered by a low-voltage level, e.g., 2.7 to 5 volts. Thus, in order to both service the high-voltage output circuits and the low-voltage logic circuits, at least two separate voltage levels, i.e., sources of electrical power or energy, must be maintained.

Since the biological tissue stimulators are designed to be utilized with a human subject, small size and independence from external power sources are strongly desired. Small batteries are commonly utilized as a source of electrical energy. Since sources of electrical energy at several voltage levels are required, either batteries of several different voltages are required, or the voltage from one set of batteries must be either stepped down or stepped up to obtain the additional voltage levels. The smaller size requirements and operating cost constraints for biological tissue stimulator mitigates against the use of batteries with a significantly higher voltage, e.g., 22.5 to 90 volts. However, the use of batteries of a lower voltage level, e.g. 1.2 to 9 volts, necessitates additional logic and control circuitry to achieve the stepped up voltage with appropriate regulation. These additional components also mitigate against small size due to their number and the increased size of the energy source (batteries) required because of the additional power they consume.

SUMMARY OF THE INVENTION

The present invention solves these problems by providing a biological tissue stimulator which requires in its most elementary forms, only a low-voltage energy source, e.g., an approximately 3-volt battery, and a step-up voltage circuit to create a high-voltage level energy source. The stimulator has a single logic circuit, e.g., a microprocessor, which is time-shared between supplying timing and amplitude signals to an output stage and supplying a switching signal to the high-voltage step-up circuit.

Thus, a biological tissue stimulator is provided having the advantageous utilization of a single low-voltage energy source, together with the time-shared utilization of an otherwise necessary logic circuitry to drive a step-up voltage circuit. The basic clocking rate and available "time-slice" is determined largely by the timing requirements of the output pulses. Since the duty cycle of stimulation pulse trains is generally low, however, considerable time is available for the logic circuitry to perform the additional task of driving the step-up voltage circuit. Thus, this function is available for "free", i.e., without additional components. Thus, a biological tissue stimulator is achieved with small size and great ease of portability.

In a preferred embodiment, the biological tissue stimulator first determines and gates the appropriate timing and amplitude characteristics to the output circuit. Following this, the stimulator then drives the step-up voltage circuit to generate the higher voltage level required. After a time, the stimulator returns to again gate timing and amplitude information to the output circuit, either the same output channel, or another, e.g., second, output channel. Following this, the stimulator again drives the step-up voltage circuit. Subsequently, the stimulator again gates timing and amplitude characteristics to an output channel, and so on. A storage mechanism stores the generated high-voltage energy until it can be used by an output stage. A voltage regulator circuit determines when the high-voltage storage level has reached a maximum, or a predetermined threshhold, at which point the stimulator then goes to an idle state to conserve power while awaiting the next required output stage gating.

A biological tissue stimulator constructed in this manner achieves significant economies of circuit component count and therefore of size, weight, power and cost. The biological tissue stimulator also minimizes the number of voltage source levels required and therefore minimizes size, weight, power and cost. Further, the biological tissue stimulator achieves economies of power consumption, thus, increasing the operating time between battery changes and decreasing the size required for the battery system.

Particularly, the present invention provides a biological tissue stimulator which has a low-voltage power source and a step-up voltage mechanism coupled to the low-voltage power source for converting the low-voltage power source to a high-voltage output. A high-voltage storage mechanism is coupled to the high-voltage output for storing the energy of the high-voltage output. A timing mechanism powered by the low-voltage power source alternately supplies a series of timing signals and supplies switching signals to the step-up voltage mechanism. An output circuit mechanism is coupled to the high-voltage output from the high-voltage storage mechanism and to the plurality of timing signals from the timing mechanism for providing a biological tissue stimulation pulse from the high-voltage output in response to the plurality of timing signals.

In a preferred embodiment, the step-up voltage mechanism is a switched-inductor circuit. In a preferred embodiment, the switched inductor circuit has an inductor coupled in series with the low-voltage power source and a switching element coupled in series with the inductor for selectively coupling the inductor to electrical ground in response to the switching signal from the timing mechanism. A rectification mechanism is coupled between the inductor and the switching element for allowing that current which flows through the rectification mechanism to flow only from the inductor. A connection mechanism couples the rectification mechanism and the high-voltage storage mechanism together.

In an alternative embodiment of the present invention, a biological tissue stimulator has a low-voltage power source and a step-up voltage mechanism coupled to the low-voltage power source for converting the low-voltage power source to a high-voltage output in response to switching signals. An output circuit is coupled to the step-up voltage mechanism for generating a biological tissue stimulation current pulse from timing signals. A mode control mechanism is coupled to the step-up voltage mechanism and the output circuit for controlling the biological tissue stimulator alternately in a pulse output mode as needed to supply the timing signals to the output circuit, and in a high-voltage generation mode when not needed in the pulse output mode to supply the switching signals to the step-up voltage mechanism. In a preferred embodiment, the biological tissue stimulator further has an idle mode to conserve the low-voltage power source when the biological stimulator is not needed in either the pulse output mode nor the high-voltage generation mode.

BRIEF DESCRIPTION OF THE DRAWINGS

The foregoing advantages, operation and construction of the present invention will become more readily apparent from reference to the following description and accompanying drawings in which.

DETAILED DESCRIPTION OF THE PREFERRED EMBODIMENTS

Figure 1:
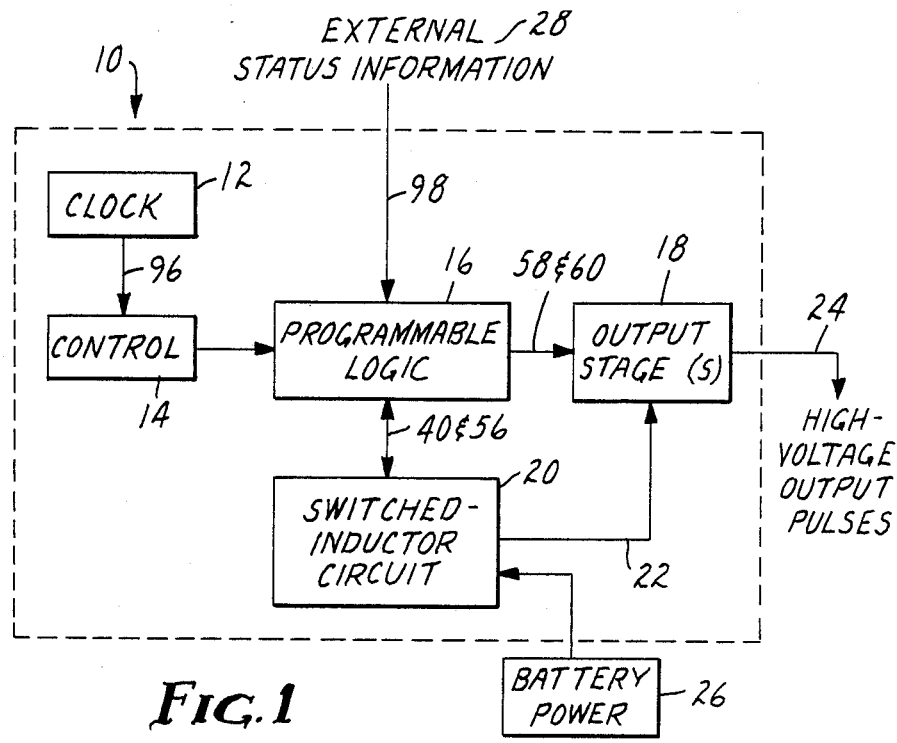
FIG. 1 is a block diagram of a biological tissue stimulator of the present invention showing time-shared programmable logic.
Figure 2:
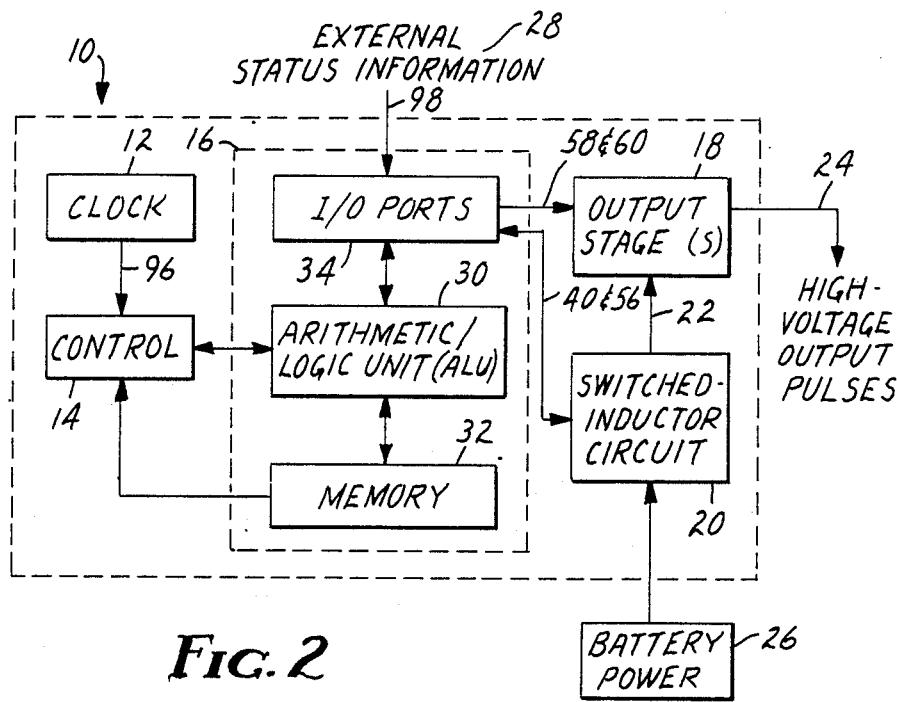
FIG. 2 is a block diagram of a biological tissue stimulator of the present invention showing detail of the programmable logic.
Figure 7:
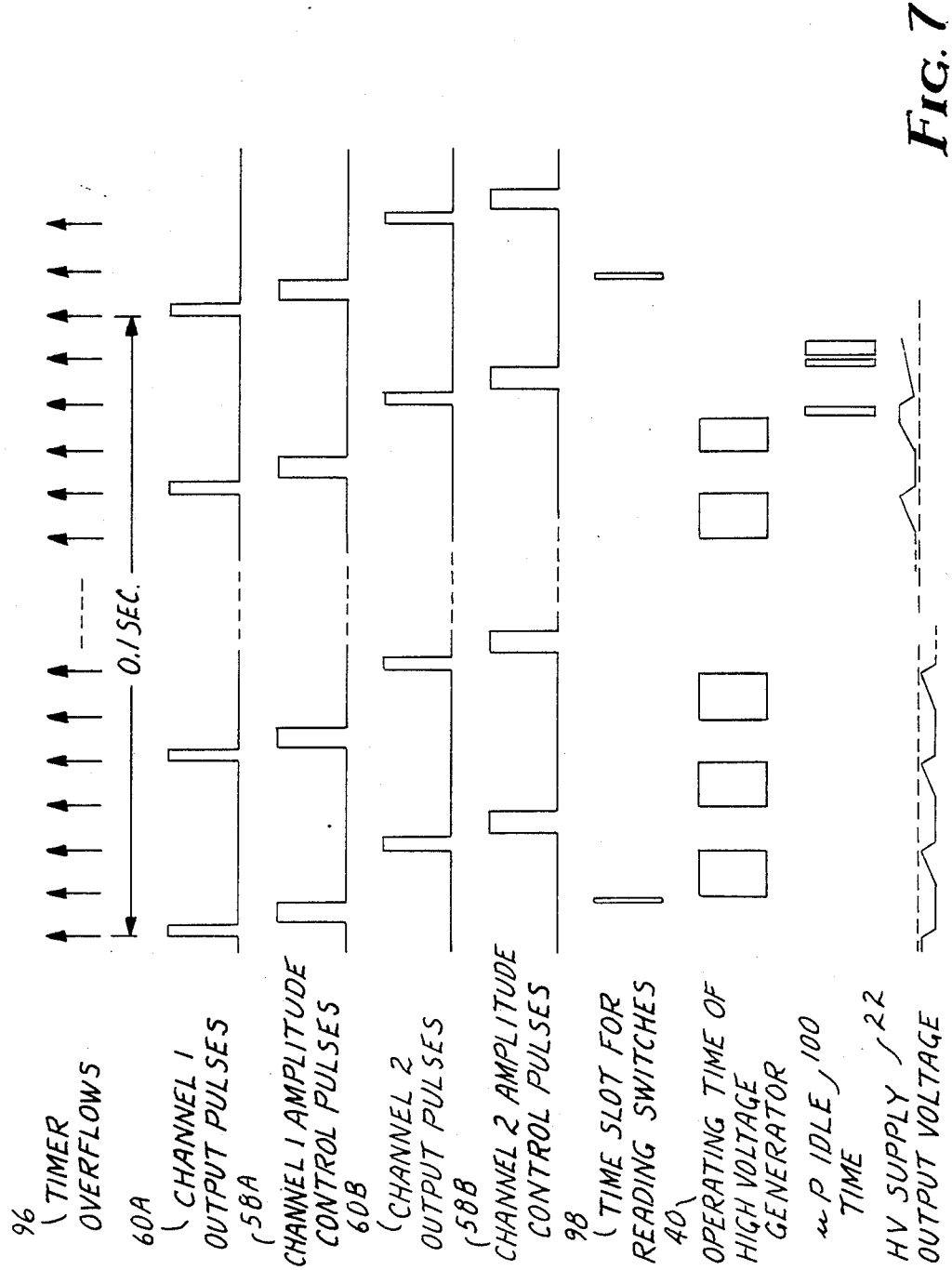
FIG. 7 illustrates timing diagrams of outputs of the programmable logic circuit of the biological stimulator of the present invention.
Figure 8:
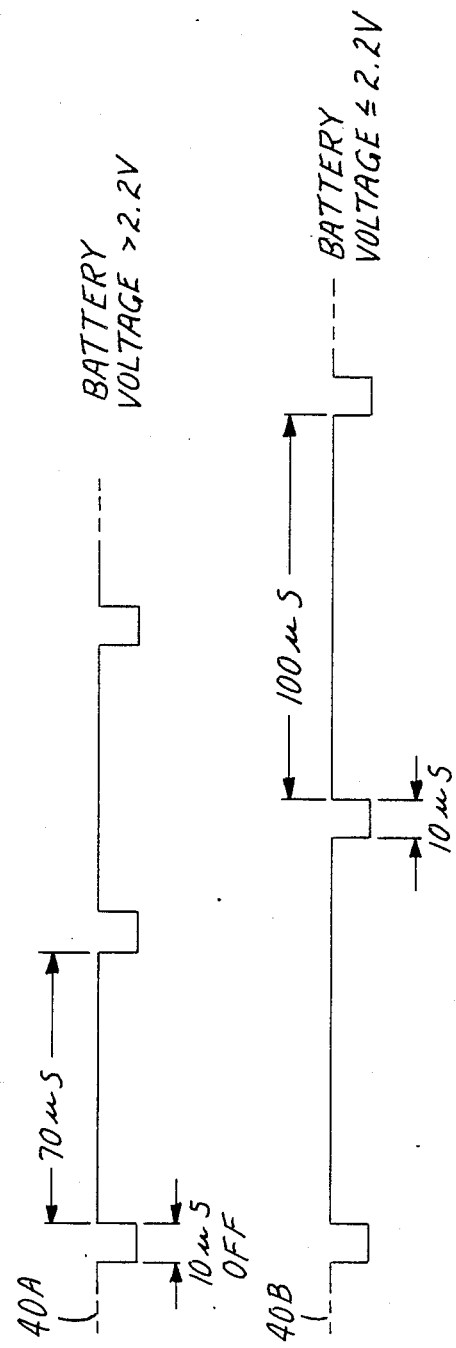
FIG. 8 illustrates timing diagrams of timing signals driving the step-up voltage circuit.

FIGS. 1 and 2 illustrate block diagrams of the biological tissue stimulator 10. A clock 12 supplies basic timing signals to a control circuit 14 which controls programmable logic block 16. Programmable logic block 16 operates on a time-shared basis between supplying timing and amplitude information (58 & 60) to output stage 18 and a switching signal 40 to step-up voltage circuit 20. The high-voltage output signal 22 is also utilized by output stage 18 to supply high-voltage output pulses 24 for use by the patient or subject receiving biological tissue stimulation pulses from the biological tissue stimulator 10. A low-voltage source of battery power 26 is shown coupled to the step-up voltage circuit 20. Programmable logic circuit 16 also receives external status information 28 which is expected to be in the form of operator controlled amplitude or mode select switches. In FIG. 2, programmable logic circuit 16 is shown as consisting of conventional arithmetic logic unit (ALU) 30, appropriate memory storage elements 32, and input-output ports 34. Such blocks and circuits are conventional in nature and the construction and operation of programmable logic block 16 in conjunction with control 14 and clock 12 will become readily apparent later in the discussion of FIGS. 7 and 8 illustrating timing diagrams.

In the biological tissue stimulator 10, the single programmable logic block 16 is time-shared between the output timing and amplitude considerations and directly driving the step-up voltage circuit 20. Since only a single low-voltage level battery source 26 is required, battery source 26 could supply not only the source of low-voltage to step-up voltage circuit 20, to be converted to a high-voltage level, but could also advantageously supply the low-voltage level power required by the logic elements contained within clock 12, control 14, programmable logic 16, and a portion of output stage 18. In the preferred embodiment, a single source of battery power 26 supplies both of these functions. Alternatively, separate battery sources 26 could supply (1) the step-up voltage circuit 20 and (2) the power for the low level logic circuits. However, it is noted that only a single low-voltage level power source is required whether it comes physically from one battery element or a plurality of battery elements. Of course, it is also possible to power all logic elements from a separate, regulated, low-voltage power supply connected to the basic low-voltage power source, i.e. the batteries.

Since programmable logic block 16 is time-shared between output stage 18 and step-up voltage circuit 20, programmable logic block 16 will at one instant of time be supplying the timing and amplitude characteristics of the output pulses 24 to the output stage 18 and at another instant of time driving step-up voltage circuit 20 to create the high-voltage output 22. Since the basic rate of signals from clock 12 is at least partially determined by the timing requirements of the short duty-cycle, high-voltage stimulation pulses 24, "time" is available for programmable logic block 16 to perform the additional task of driving the step-up voltage circuit 20. Thus, the task of driving the step-up voltage circuit 20 is achieved essentially for "free".

Although a single output stage 18 is illustrated in FIGS. 1 and 2, it is to be recognized and understood that the high-voltage level 22 from step-up voltage circuit 20 could be supplied to a plurality of output stages 18 and that programmable logic block 16 could be additionally time-shared to supply timing and amplitude characteristics to the high-voltage output pulses 24 to be delivered by the additional output stages 18.

Figure 3:
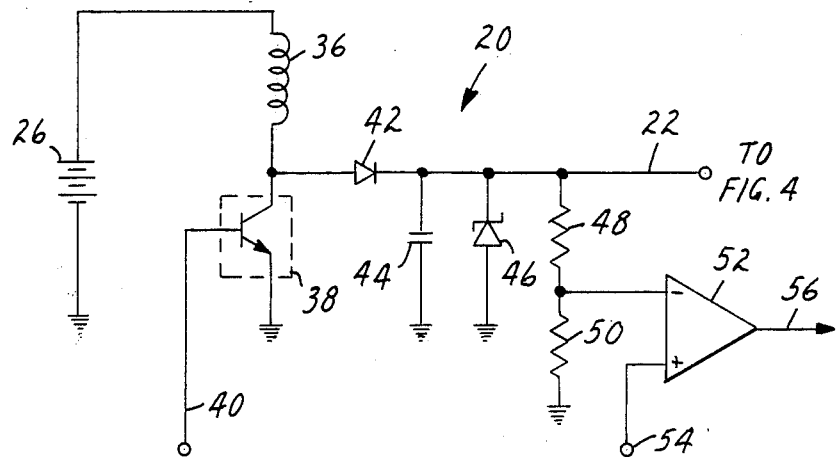
FIG. 3 is a detailed circuit diagram of the high-voltage step-up circuit of the biological tissue stimulator of the present invention.

Step-up voltage circuit 20 is shown in a detailed schematic in FIG. 3. An inductor 36 is connected to one end of the low-voltage power source, battery, 26. In a preferred embodiment, inductor 36 is a one millihenry inductor and battery 26 are two size "AAA" batteries in series supplying a voltage level of 2-3 volts. The opposite end of inductor 36 is coupled through a high-voltage gate, or switching circuit, 38 coupled to electrical ground. Gate 38 is driven by switching signal 40 supplied from programmable logic block 16 (in FIGS. 1 and 2). The end of inductor 36 which is coupled to gate 38 is also coupled to the anode of diode 42 to rectify the signal received from inductor 36 and to assure that current is only retrieved from inductor 36 and not returned to it. Essentially, potential energy from battery 26 is transformed into magnetic energy within the inductor 36 when gate 38 is momentarily opened, i.e., transistor gate 38 is conducting, by the programmable logic block 16. This magnetic energy is subsequently transformed into potential energy in capacitor 44 when gate 38 is closed, i.e., transistor gate 38 is not conducting. The current passes through diode 42 and is stored in capacitor 44, operating as a storage element, until it can be subsequently utilized by the output stage 18. The basic process of opening and closing gate 38, as controlled by switching signal 40, is repeated by the programmable logic block until the appropriate high-voltage signal 22 level is reached. A back biased zener diode 46 provides basic over-voltage protection. In a preferred embodiment zener diode 46 is an approximately 62 volt zener diode. High-voltage signal 22 is maintained at approximately 50-55 volts by a voltage regulation system consisting of resistors 48 and 50 forming a voltage divider coupled to one input of a comparator 52 whose other input terminal is a stable reference voltage source 54, which in a preferred embodiment is approximately 1.7 volts. The output 56 of comparator 52 is fed back to programmable logic block 16 for use by the programmable logic block 16 for monitoring the status of the high-voltage circuit 20 and for providing feedback so that the programmable logic unit 16 may appropriately control the mode of operation of the biological tissue simulator 10.

Figure 4:
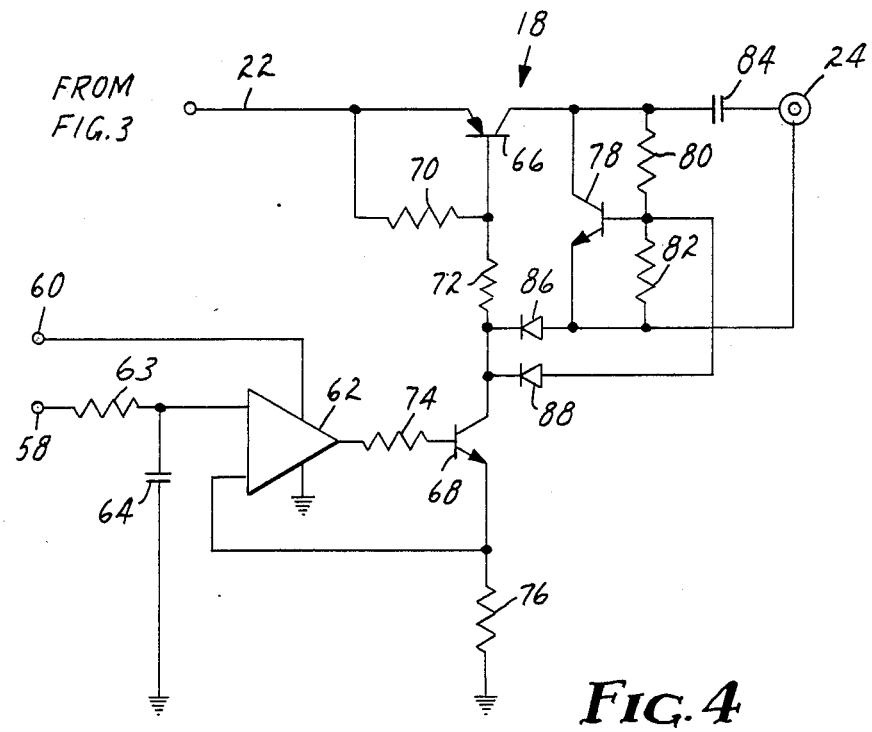
FIG. 4 is a detailed circuit diagram of an output stage of the biological tissue stimulator of the present invention.

A detailed circuit diagram of the output stage 8 of a preferred embodiment of the present invention is illustrated in FIG. 4. Amplitude signal 58, received from the programmable logic unit 16, is a pulse train with a fixed pulse repetition rate. The pulse width of each individual pulse is dependent upon the amplitude desired for the high-voltage output pulse 24 which are to be provided by the output stage 18. Output stage 18 also receives timing signal 60 from the programmable logic block 16. Timing signal 60 is activated to trigger operational amplifier 62 to initiate a high-voltage output pulse 24 from the output stage 18. Capacitor 64 and resistor 63 form a low-pass filter which essentially recovers the DC component of the variable width pulse train from amplitude signal 58. Output stage 18 also receives high-voltage signal 22 from the step-up voltage circuit 20. Transistors 66, 68 and resistors 70, 72, 74 and 76 transform the high-voltage signal 22 into a current pulse to be supplied as high-voltage output pulse 24. Transistor 78, resistors 80 and 82, and capacitor 84 ensure a zero net DC component for the output current pulse train 24. Diodes 86 and 88 permit transistor 78 to conduct only when transistor 68 is not conducting.

Figure 5:
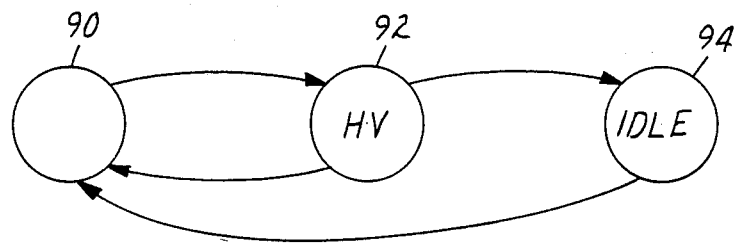
FIG. 5 illustrates a mode diagram of a biological tissue stimulator of the present invention.

FIG. 5 illustrates one preferred embodiment of the modes of operation of the biological tissue stimulator 10 of the present invention. Generally, in FIG. 5, the biological tissue stimulator is in state 90 providing amplitude and timing characteristics 58 and 60 to one of the output stages 18. When that task is completed, the biological tissue stimulator then moves to state 92 to supply switching signals 40 to a step-up voltage circuit 20 operating utilizing a switched inductor circuit which creates a high-voltage level 22 for subsequent use by the output stages 18. When the voltage level of the high-voltage supply 22 reaches the correct value, the biological tissue stimulator may then move to state 94 to "idle" in order to conserve energy from the low-voltage power source 26.

Figure 6:
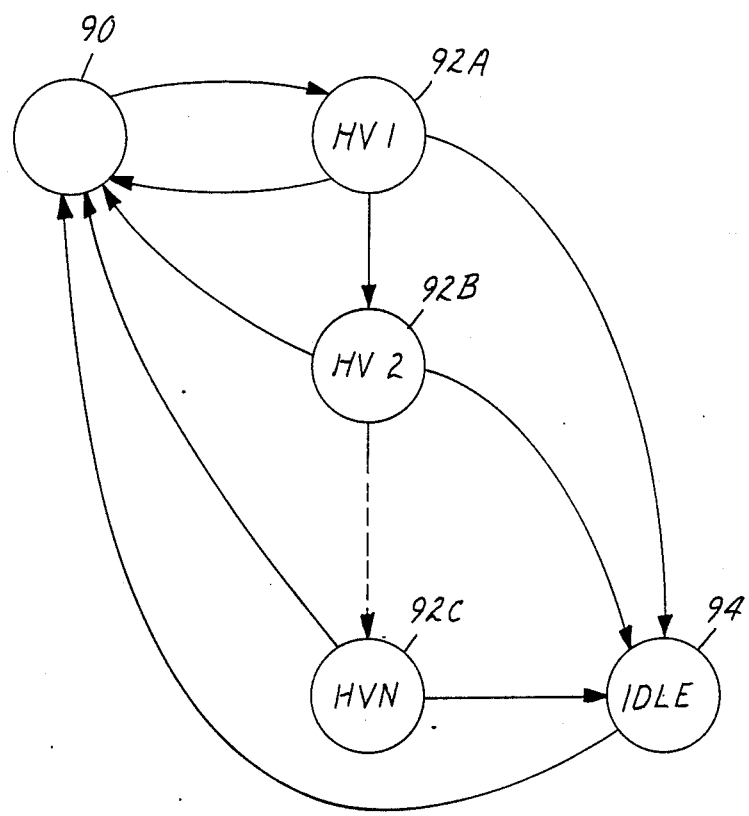
FIG. 6 illustrates a mode diagram of an alternative embodiment of the biological tissue stimulator of the present invention.

FIG. 6 shows a variation of the state diagram in FIG. 5. FIG. 6 is an alternative in which a single state 90, used to supply timing and amplitude characteristics to output stages 18 serves a plurality of high-voltage step-up circuits 20 and, hence, must individually sequentially move through states 92A, 92B to 92C to complete supplying switching signals 40 to all of the available high-voltage step-up voltage circuits 20 included in the biological tissue stimulator 10. If any time is available, again, idle state 94 is reached.

Alternatively, to the mode of operation illustrated in FIG. 6, a single step-up voltage circuit 20 may serve a plurality of output stages 18. In this case, only one step-up voltage circuit 20 is supplied with switching signals 40 while the plurality of output stages 18 are supplied timing and amplitude information again on a time-shared basis. This can be more readily illustrated from the detailed timing diagram illustrated in FIG. 7. FIG. 7 illustrates a plurality of timer overflows 96 which would be supplied from clock 12 and which represents the basic timing intervals available to programmable logic block 16. The timing diagram in FIG. 7 presumes that there are two output stages 18 given a nomenclature of channel 1 and channel 2 and a single step-up voltage circuit 20. During the first interval between timer overflows 96, channel 1 output pulse 60A is supplied immediately followed by channel 1 amplitude signal 58A. The time-averaged pulse width of amplitude signal 58A is variable and, in the output stage 18, determines the amplitude of the delivered output current pulse 24. In a preferred embodiment, immediately after supplying the channel 1 amplitude signal 58A, programmable logic block 16 will read external status information 28 as indicated by signal 98. If any time remains in the first timer overflow 96 interval, programmable logic block 16 will then start supplying switching signal 40 to step-up voltage circuit 20. In a preferred embodiment, the entire second timer overflow 96 interval, if required, is used to supply switching signal 40 to the step-up voltage circuit 20. During the third timer overflow 96 interval, channel 2 output pulse 60B and channel 2 amplitude signal 58B is supplied to the channel 2 output stage 18. Since in a preferred embodiment external status information is only read on a longer interval, programmable logic unit 16 will then move directly to supply switching signal 40 to step-up voltage circuit 20. The fourth timer overflow interval 96 is similar to the second timer overflow 96 interval in that the entire time period, if required, is spent supplying switching signal 40 to step-up voltage circuit 20. In this timing diagram, it is presumed that the high-voltage level signal 22 is lower than desired and a maximum amount of time is spent supplying switching signals 40 to build high-voltage signal level 22 up to the desired value. Further timer overflow 96 intervals are similar to those preceding until the high-voltage level supply 22 reaches its maximum level, or its predetermined threshhold level. At this time, programmable logic block 16 instead of continuing to supply switching signals 40 to the step-up voltage circuit 20 will instead go to the idle state as evidenced by idle blocks 100 since this time is not required to maintain the high-voltage supply level 22. Also, on a periodic basis, another time slot 98 is reserved for reading external status information 28.

FIG. 8 illustrates a preferred timing diagram of the switching signal 40 to be supplied to step-up voltage circuit 20. The exact period of time that gate 38 is to be opened and closed ideally should depend upon the magnitude of the inductance of inductor 36, desired efficiency levels (reflecting power losses in major components), output current requirements and, most significantly, the voltage supplied by battery 26. Since battery voltage is not an operational constant, the timing diagrams illustrated in FIG. 8 adjust depending upon the voltage level. Generally, as the batteries 26 discharge, their voltage level will decrease. In general, gate 38 should not be open past the point of inductor 36 saturation since power losses will increase greatly at this point. However, gate 38 should still be open long enough to build sufficient energy storage in the inductor. Magnetic energy increases with the square of the peak current through the inductor. The voltage supplied from batteries 26 is approximately equal to the value of the inductance in the inductor 36 times the quantity, the change in current divided by the change in time. In order to maintain the change in current constant as the battery voltage decreases, the change in time, or the amount of time the gate 38 is closed, must increase. It is generally important to keep the peak current rather constant in order to maintain the power capacity of the high-voltage signal level 22 while limiting the time the switched inductor circuit must be operated. In other words, the "time-slice" required from the programmable logic block 16 remains well-bounded despite changes in battery 26 voltage. The time that gate 38 is open is preferred to be a function of the battery 26 voltage. This is illustrated in the timing diagrams of switching signal 40 illustrated in FIG. 8. In a preferred embodiment, two discrete timing signals are supplied. Switching signal 40A is supplied when the battery voltage is greater than 2.2 volts. The timing diagram of switching signal 40A indicates that switching signal 40A is "on" (causing gate 38 not to conduct) for 10 microseconds. When the battery voltage drops below 2.2 volts, switching signal 40B is then utilized. In order to maintain proper current levels, the "on" time of switching signal 40 is increased to 100 microseconds. However the "off" time remains constant at 10 microseconds. The "on" time of switching signal 40 is varied in order to get peak operation from inductor 36 while the "off" time of switching signal 40 is kept constant since this amount of time is only necessary to get the current out of the inductor into the capacitor 44 to store the current as a voltage available as high-voltage signal level 22.

Thus, there has been shown and described a novel biological tissue stimulator with time-shared logic driving both output timing and a high-voltage step-up circuit. It is to be recognized and understood, however, that various changes, modifications, and substitution in the form and in the details of the present invention may be made by those skilled in the art without departing from the scope of the following claims.

What is claimed is:

1. A biological tissue stimulator, comprising:
   a low-voltage direct current power source;
   step-up voltage means operatively coupled to said low-voltage direct current power source for converting said low-voltage direct current power source to a high-voltage direct current output;
   said step-up voltage means having high-voltage storage means coupled to said high-voltage direct current output for storing the voltage of said high-voltage direct current output;
   timing means powered by said low-voltage direct current power source for automatically alternately supplying a plurality of switching signals to said step-up voltage means and supplying a plurality of timing signals; and
   output circuit means operatively coupled to said high-voltage storage means and to said timing means for providing a biological tissue stimulation pulse from said high-voltage direct current output in response to said plurality of timing signals.

2. A biological tissue stimulator as in claim 1 in which said step-up voltage means also has a regulating means operatively coupled to said high-voltage storage means and said timing means for disabling said switching signals to said step-up voltage means when said high voltage storage means has achieved a predetermined voltage level.

3. A biological tissue stimulator as in claim 2 wherein said step-up voltage means includes a switched-inductor circuit means for stepping up said low-voltage direct current power source.

4. A biological tissue stimulator as in claim 3 wherein said output circuit means comprises a voltage-to-current convertor and said biological tissue stimulation pulse is a current pulse.

5. A biological tissue stimulator as in claim 4 wherein said output circuit means includes means providing said biological tissue stimulation pulse which varies in current amplitude in direct response to the pulse width of one of said timing signals from said timing means.

6. A biological tissue stimulator as in claim 3 wherein said switched-inductor circuit means comprises:
   an inductor coupled in series with said low-voltage direct current power source;
   switching means coupled in series with said inductor and said low-voltage direct current power source for selectively coupling said inductor across said low-voltage direct current power source in response to said switching signal for said timing means; and
   rectification means coupled between said inductor and said high-voltage storage means for allowing that current which flows through said rectification means to flow only from said inductor and be stored in said high-voltage storage means.

7. A biological tissue stimulator, comprising:
   a low-voltage direct current power source;
   step-up voltage means coupled to said low-voltage direct current power source for converting said low-voltage direct current power source to a high-voltage direct current responsive to switching signals;

said step-up voltage means having high-voltage storage means coupled to said high-voltage direct current output for storing the voltage of said high-voltage direct current output;

output circuit means coupled to said high-voltage storage means for generating a biological tissue stimulation current pulse responsive to timing signals; and mode control means coupled to said step-up voltage means and said output circuit means for alternately supplying as needed, in a pulse output mode, said timing signals to said output circuit means, and, in a high-voltage generation mode, said switching signals to said step-up voltage means.

8. A biological stimulator as in claim 13 wherein said mode control means includes means for conserving said low-voltage direct current power when not needed in either said pulse output mode nor in said high-voltage generation mode.

9. A biological tissue stimulator, comprising:

a low-voltage power source;

step-up voltage means coupled to said low-voltage power source for converting said low-voltage power source to a high-voltage output responsive to switching signals;

said step-up voltage means having high-voltage storage means coupled to said high-voltage output for storing the energy of said high-voltage output;

output circuit means coupled to said high-voltage storage means for generating a biological tissue stimulation current pulse responsive to timing signals;

mode control means coupled to said step-up voltage means and said output circuit means for alternately supplying as needed, in a pulse output mode, said timing signals to said output circuit means, and, in a high-voltage generation mode, said switching signals to said step-up voltage means, and in an idle mode, conserving said low-voltage power source when not needed in either of said pulse output mode nor in said high-voltage generation mode; and regulating means operatively coupled to said high-voltage storage means and said mode control for disabling said switching signals to said step-up voltage means when said high-voltage storage means has achieved a predetermined voltage level.

10. A biological tissue stimulator as in claim 9 wherein said step-up voltage means includes a switched-inductor circuit for stepping up said low-voltage power source.

* * * * *